United States Patent

Conrad et al.

[11] Patent Number: 6,153,111
[45] Date of Patent: Nov. 28, 2000

[54] METHOD AND APPARATUS FOR PURIFYING WATER

[75] Inventors: Wayne Ernest Conrad; Helmut Gerhard Conrad; Ted Szylowiec, all of Hampton, Canada

[73] Assignee: Fantom Technologies Inc., Welland, Canada

[21] Appl. No.: 09/240,619

[22] Filed: Feb. 1, 1999

[30] Foreign Application Priority Data

Nov. 9, 1998 [CA] Canada ................................. 2253689

[51] Int. Cl.⁷ ........................................................ C02F 1/78
[52] U.S. Cl. .................. 210/741; 210/760; 261/DIG. 42
[58] Field of Search .................................. 210/760, 739, 210/741, 750, 120; 222/61; 261/DIG. 42

[56] References Cited

U.S. PATENT DOCUMENTS

| | | | |
|---|---|---|---|
| 3,699,776 | 10/1972 | La Raus | 62/157 |
| 4,453,953 | 6/1984 | Tanaka et al. | 55/163 |
| 5,053,140 | 10/1991 | Hurst | 210/202 |
| 5,116,574 | 5/1992 | Pearson | 210/760 |
| 5,213,773 | 5/1993 | Burris | 422/256 |
| 5,547,584 | 8/1996 | Capehart | 210/760 |
| 5,683,576 | 11/1997 | Olsen | 210/138 |
| 5,971,368 | 10/1999 | Nelson et al. | 261/64.3 |

FOREIGN PATENT DOCUMENTS 5155967  1/1995  Japan .
6071199  10/1995  Japan .

*Primary Examiner*—David A. Simmons
*Assistant Examiner*—Frank M. Lawrence
*Attorney, Agent, or Firm*—Philip C. Mendes da Costa; Bereskin & Parr

[57] ABSTRACT

A method for treating a liquid such as water with a gas such as ozone where the liquid to be treated is introduced into a treatment vessel, gas is introduced into the treatment vessel to treat the liquid and the liquid is treated. The treatment vessel is then pressurized and the pressure in the treatment vessel is used to dispense the treated liquid from the treatment vessel through a filter.

24 Claims, 1 Drawing Sheet

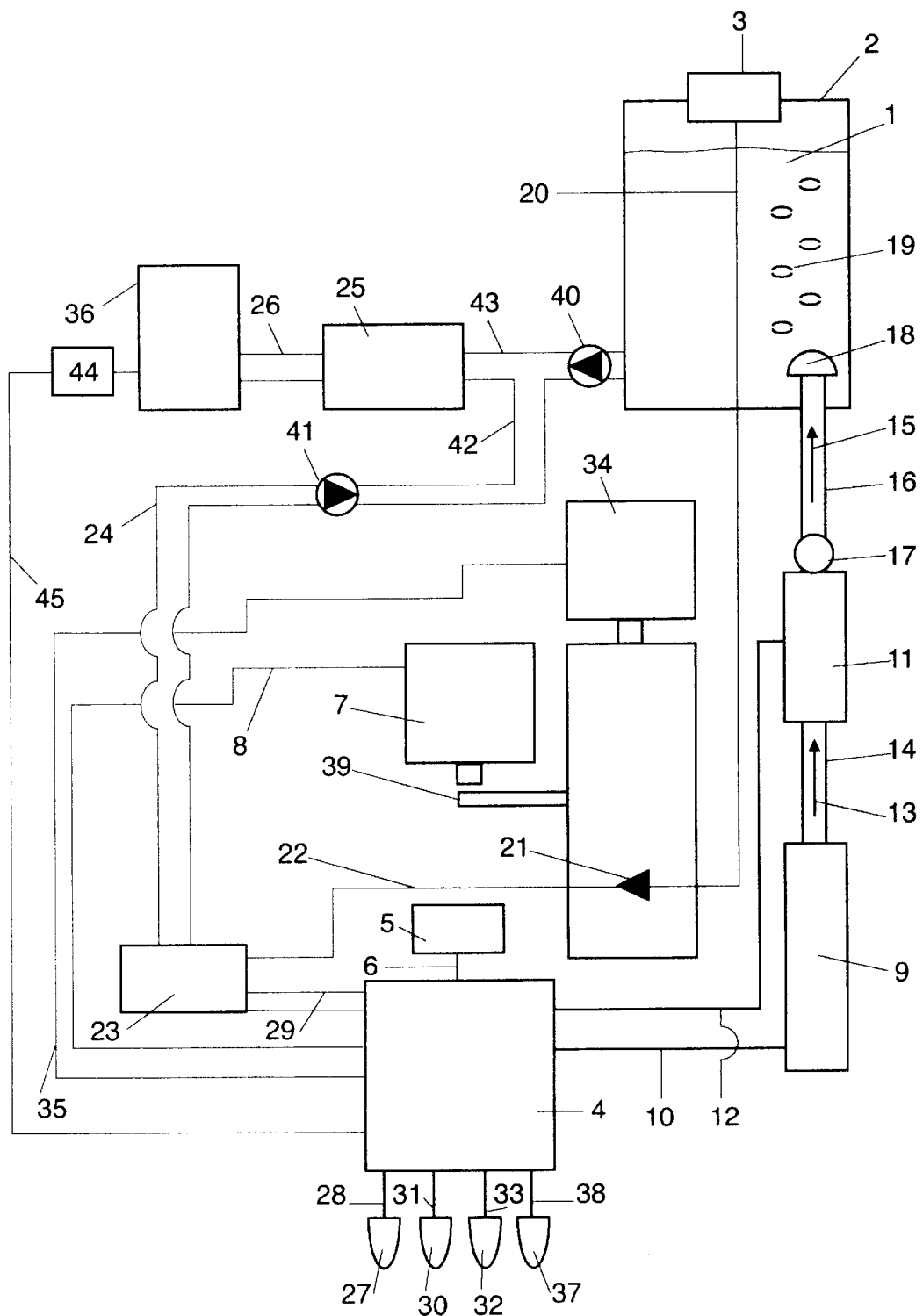

METHOD AND APPARATUS FOR PURIFYING WATER

FIELD OF THE INVENTION

This invention relates of an apparatus for treating water with a gas containing ozone. The apparatus may be used in the production of water fit for human consumption from water contaminated by microorganisms, chemicals, heavy metals and minerals. The gas containing ozone may be present either by itself or in combination with one or more other gasses and/or a liquid. Further, the water may be present by itself or may also have one or more liquids and/or one or more other gases associated therewith.

BACKGROUND OF THE INVENTION

The production of water suitable for human consumption from water contaminated by one or more of microorganisms, chemicals, heavy metals and minerals is a requirement throughout the world. Many different proposals have been made for the purification of contaminated water.

A popular system in widespread use for the purification of contaminated water is a filtration based system. Such systems use a filter made from a combination of a porous media filter, activated carbon, and an ion exchange resin through which the contaminated water is passed. The filtered water is typically fed into a clean water reservoir. This type of system will reduce the levels of chlorine, lead, and pesticides. However, there are several disadvantages associated with this device.

The first disadvantage of this water purification system is that the structure of the filter provides a breeding ground for microorganisms thereby multiplying the dangers of microorganisms which may be present in very low numbers. Another disadvantage of such a water purification system is that the filter life is not measured and it is possible for the user to employ the filter beyond its useful life. A further disadvantage of such a water purification system is that oils and fuels often present in water drawn from lakes and rivers are not readily removed. Further, these oils and fuels tend to coat the filters and damage their operational life and effectiveness. Some filtration based products now incorporate a means of measuring the water volume passing though the filter and an indicator as to when to change the filter. Other filters incorporate an iodine product to minimize the risk of microbiological hazards, however, these materials often impart undesirable tastes and many are potential carcinogens.

Another popular system in use for the purification of contaminated water is a system which employs ultraviolet light for disinfection in series with a porous media and carbon filter. This type of system will reduce the levels of chlorine, lead, and pesticides and has some disinfection capability. One disadvantage with this system is that the ultraviolet light's disinfection efficacy is greatly diminished by turbidity or color in the water which can cause the filter to become contaminated by microorganisms which can readily live and breed therein thereby multiplying the danger from any microorganisms which may be present. Thus, the filter of this system also suffers from the disadvantages associated with filters of filtration based systems.

Contaminated water may also be treated to obtain drinking water by passing ozone through the water to kill microorganism contaminants such as bacteria present in the water. Various processes to treat water have been developed using combinations of filtration and ozonation.

For example, U.S. Pat. No. 5,683,576 to Olsen describes an apparatus for treating contaminated water by passing ozone through the water. In the system disclosed by Olsen, an ozone containing gas is passed through the water to be treated, until the instantaneous concentration of ozone in the head space above the water being treated reaches a predetermined level. Then, the flow of ozone through the water continues for a predetermined period of time.

The amount of ozone which must be passed through the water to purify it to any particular state will vary depending upon the initial quality of water to be treated. For example, untreated well or lake water may require a higher degree of purification than treated city water which has previously been treated to some degree.

One disadvantage of Olsen is that it can not be reliable used with such disparate types of water supply. Olsen does not monitor the total amount of ozone which passes through the water unreacted. Thus, the actual degree of treatment of the water is not measured. The system is designed only to ensure that a predetermined minimum amount of ozone passes through the system unreacted. The system makes the assumption that once the concentration of ozone reaches the predetermined level, that it does not subsequently drop below that level, or rise above that level. Further, it assumes that once the water to be. treated has been exposed to the preset ozone concentration for a predetermined time that the water is suitable for use. However, depending on the degree of contamination of the water to be treated, the time required to treat the material will vary.

In Olsen, the amount of unreacted ozone passing through the system prior to the time when the instantaneous concentration reaches the predetermined level is not measured. Further, the amount of unreacted ozone passing through the system measured during the predetermined amount of time after the predetermined instantaneous concentration is reached is not measured. Thus, the actual degree of treatment of the water is not measured.

SUMMARY OF THE INVENTION

In accordance with the instant invention, there is provided a method of treating a liquid comprising water with a gas comprising ozone, the method comprising the steps of:

(a) providing the liquid in a treatment vessel;

(b) introducing the gas into the-vessel to treat the liquid in the treatment vessel to obtain treated liquid;

(c) increasing the pressure in the treatment vessel; and (d) utilizing the increased pressure in the treatment vessel to dispense the treated liquid from the treatment vessel.

In one embodiment, the method further comprises the step of venting at least a portion of the gas from the treatment vessel during step (b). The pressure in the treatment vessel is preferably increased by reducing the amount of gas which is being vented from the treatment vessel.

In another embodiment, the method further comprises the step of passing the treated liquid through a filter located downstream from the treatment vessel during step (d). At least a portion of the gas vented from the treatment vessel during step (b) may be passed through the filter, and preferably all of the vented off gas is passed through the filter.

One advantage of this method is that the ozone which remains in the off gas may be used to treat the filter and reduce or prevent the growth of microorganisms in the filter. Therefore, it is preferred that all or essentially all of the gas introduced into the treatment vessel is passed through the filter during the treatment cycle. However, during the initial stages of the treatment cycle, the treatment vessel may be sealed (i.e. some or all of the off gas maybe retained in the vessel) to increase the operating pressure of the treatment vessel. Once a desired pressure is achieved, the off gasses may be vented to treat the filter while maintaining the treatment vessel at the elevated pressure.

In another embodiment, the method further comprises the step of automatically dispensing the treated water when the pressure in the treatment vessel reaches a preset level.

In another embodiment, the method further comprises step of introducing the gas into the treatment vessel as bubbles.

In another embodiment, the method further comprises the step of treating the liquid with the gas until a prespecified condition is met, the prespecified condition selected from the group:

(a) until a predetermined level of treatment of the liquid is achieved, or (b) for a predetermined time, or (c) until the treatment of the liquid does not match a preset treatment profile.

A user may be signalled if a predetermined level of treatment of the liquid is not achieved in the predetermined time or if the treatment profile is not achieved. This may be achieved by measuring the ozone concentration in the off gas in the treatment vessel and signalling the user if the concentration of ozone in the off gas is higher than that of the treatment profile. Alternately, or in addition, the user may be signalled if the concentration of ozone in the off gas is lower than that of the treatment profile.

In an other embodiment, the method further comprises the step of monitoring the treatment of the liquid and preventing the liquid from being dispensed from the treatment vessel if a predetermined level of treatment of the liquid is not achieved.

In accordance with another embodiment of the instant invention, there is provided an apparatus for treating a liquid comprising water with a gas comprising ozone, the apparatus comprising:

(a) a treatment vessel having at least one inlet port for introducing the gas and the liquid into the vessel and, a gas outlet port for removing gas from the vessel;

(b) a pressurized source of the gas for treating the liquid in communication with gas inlet port;

(c) a first passageway for dispensing treated liquid from the treatment vessel during a dispensing cycle, the passageway having a first valve operable between a first open position and a second closed position;

(d) a second valve associated the gas outlet port and having a first open position for allowing the off gas to vent from the treatment vessel and a second open position for preventing the off gas to vent from the treatment vessel whereby when the pressure in the treatment vessel reaches a predetermined level, the first valve automatically moves to the open position to cause treated liquid to flow from the treatment vessel through the first passageway.

In one embodiment, the apparatus further comprises a filter positioned downstream from -the treatment vessel and the predetermined pressure level is determined based on the pressure required to cause the treated water to flow through the filter. The apparatus may have a second passageway in flow communication with the second valve and the filter for venting the off gas through the filter.

In another embodiment, the liquid in the treatment vessel is subjected to a treatment cycle and at the end of the cycle, the second valve is moved towards the closed position to increase the pressure in the treatment vessel to the predetermined level. The second valve may be a pressure actuated valve such as a spring actuated valve or a check valve. Alternately, the valve may be electronically controlled by a controller and the apparatus may include a pressure sensor for monitoring the pressure in the treatment vessel and signalling the controller when a predetermined pressure is reached.

In another embodiment, the apparatus further comprises an ozone generator located in flow communication with the inlet port. In addition, the apparatus may further comprise an oxygen concentrator located upstream of and in flow communication with the generator.

In another embodiment, the apparatus further comprises a controller for monitoring the treatment of the water in the treatment vessel with the gas until a prespecified condition is met, the prespecified condition selected from the group:

(a) until a predetermined level of treatment of the liquid is achieved, or (b) for a predetermined time, or (c) until the treatment of the liquid does not match a preset treatment profile.

In one embodiment, the apparatus further comprises a warning signal to advise a user if a predetermined level of treatment of the liquid is not achieved in the predetermined time or if the treatment profile is not achieved. The apparatus may have a sensor for measuring the ozone concentration in the off gas in the treatment vessel and a warning signal for advising a user if the concentration of ozone in the off gas is higher than that of the treatment profile. Alternately, or in addition, the apparatus may have a warning signal for advising a user if the concentration of ozone in the off gas is lower than that of the treatment profile.

In another embodiment, the apparatus further comprises an actuator for commencing the dispensing cycle, a controller for monitoring the treatment of the liquid and preventing the liquid from being dispensed from the treatment vessel if a predetermined level of treatment of the liquid is not achieved.

In accordance with another embodiment of the instant invention, there is provided an apparatus for treating a liquid comprising water with a gas comprising ozone, the apparatus comprising:

(a) retaining means for retaining the liquid during a treatment cycle of the liquid with the gas;

(b) means for introducing the gas under pressure into the retaining means to obtain treated liquid;

(c) venting means for removing off gas from the retaining means;

(d) means for increasing the pressure in the retaining means at the end of a treatment cycle; and, (e) dispensing means for automatically removing treated liquid from the retaining means during a dispensing cycle when the pressure in the retaining means reaches a predetermined level.

At the end of the treatment cycle, the venting means may be interrupted (eg. closed) to increase the pressure in the retaining means to the predetermined level.

In one embodiment, the apparatus further comprises means for actuating the dispensing cycle and means for preventing the liquid to be dispensed from the retaining means if a predetermined level of treatment of the liquid is not achieved.

BRIEF DESCRIPTION OF THE DRAWINGS

A further, detailed description of the invention, briefly described above, will follow by reference to the following drawings of a preferred embodiment of the invention in which:

FIG. 1 shows a schematic representation of an apparatus according to the instant invention.

DESCRIPTION OF PREFERRED EMBODIMENT

FIG. 1 schematically illustrates a system for treating a liquid comprising water with a gas comprising ozone. Preferably the liquid consists of water and the gas comprises air containing ozone. Accordingly, the apparatus may be used for purifying and disinfecting water by means of ozone gas. The method and apparatus may be used in particular in a domestic setting for treating water prior to its use in a residence.

Water 1 is introduced into container 2 (which may be of any particular size and shape) through an inlet port, for example a resealable cap 3. The cap 3 may be removably affixed to the container 2 by any suitable method, such as a screw thread or a bayonet mount. When the cap is closed, the container is sealed.

It will be appreciated that container 2 may allow some of the gas to escape there from during the treatment of water 1 (eg. some of the treatment gas may exit container 2 during the treatment). In such an embodiment, the inlet port may only be partially sealed. Alternately all, or essentially all, of the fluid may be maintained in container 2 until the treatment cycle is completed and in such a case, the liquid inlet port is fully sealable.

The unit is provided with a source of ozone. This may be a canister of compressed ozone gas which is provided as part of the unit or fed to container 1 via a hose (not shown). Preferably, the device includes an ozone generator and the ozone generator is supplied with a source of oxygen. This source of oxygen may be the ambient air. Preferably, oxygen enriched air is used. Accordingly, the unit may be connected to a source of oxygen enriched air for example the unit may be provided with a canister of compressed gas containing elevated levels of oxygen or pure oxygen, or it may be connected via a hose to such a source or, preferably, the unit may include an oxygen concentrator 9, such as those which utilize pressure swing adsorption and are known in the art. Pressurized air may be provided to oxygen concentrator 9 such as by a motor driven fan, or any other manner known in the art (not shown).The The control circuit 4 of this device derives power from any power source, eg. from a battery 5, by means of wire 6. The power source could also be, for example, a regular electrical outlet. A user may activate the unit by pressing the start button which sends a signal to the control circuit 4 through the wire 8.

When a cycle is initiated by pressing the start button, an off gas flow control valve 21 is opened, preferably by mechanical means. Preferably, the control valve 21 is opened through use of a lever 39, although any suitable device may be used. Further, upon initiation of a cycle, control circuit 4 preferably begins to time the cycle. Optionally, power light 27 is turned on by means of wire 28, to indicate that a cycle has been initiated.

When the unit is activated, ozone is provided to treat water 1. If the unit includes an oxygen concentrator 9 and an ozone generator 11 control circuit 4 provides power to oxygen concentrator 9 through wire 10. The pressurized gas containing oxygen 13 then flows from the oxygen rich gas source 9 through tube 14 and into ozone generator 11 where at least a fraction of the oxygen present is converted to ozone to produce ozone oxygen mixture 15. Ozone generator 11 may any ozone generator which is known in the art. This ozone oxygen mixture 15 generated by the ozone generator then flows through a pipe 16, through a one way check 17 and into the container 2. The gas may enter the container 2 through a sparger 18 which serves to disperse the gas into fine bubbles 19. It will be appreciated that water 1 and mixture 15 may be introduced into container 2 by any method known in the art. For example, water may be introduced to container 2 via an inlet port which has a water supply (eg a hose) affixable thereto. Alternately, water 1 and mixture 2 may be introduced, either sequentially or concurrently or a combination thereof, into container 2 via a single inlet port.

After passing through the water 1 in the container 2, the gas exits the container 2 through a vent line 20. This removes gas from the head space in container 2 and prevents pressure from building up in the container 2. The vented gas passes through the off gas flow control valve 21 and through tube 22, and into the ozone off gas sensor 23. It then passes through pipe 24, and check valve 41 into tube 42. The vented gas then passes through tube 43 and filter 25 and into a treated water carafe 36 via tube 26 from where it may pass into the room as oxygen rich gas. Thus, the ozone off gas may serve to disinfect the filter 25 and prevent microbiological growth within the filter. Filter 25 may be any filter known in the water filtration art. Preferably, filter 25 comprises carbon.

It will be appreciated that if container 2 is at least partially sealed, eg. valve 21 is closed or at least partially closed, that pressure will build up in container 2. The increase in pressure in container 2 is beneficial in the treatment of water 1 by mixture 15. In such a case, a bleed stream of the off gases may be passed to sensor 23. Alternately, once the pressure has built up to a desired level in container 2, a steady flow of off gasses may be removed from container 21 to prevent further pressure build up in container 2.

Signals from the ozone sensor 23 are transmitted to the control circuit by any means, for example a wire 29. The control circuit 4 monitors the ozone off gas concentration by means of sensor 23.

Ozone sensor 23 measures the level of ozone in the off gas by any of those known in the art. The ozone level may be measured on an intermittent basis as water 1 is treated but is preferably continuously monitored. Control circuit 4 may be programmed with a preset valve corresponding to an amount of ozone which must be measured by sensor 23 for water 1 to be treated to a desired level. Alternately, control circuit 4 may be programmed with a concentration/time profile (ie. the treatment profile) of ozone in the off gas which must be measured by sensor 23 for water 1 to be treated to a desired level. In the latter case, during the treatment cycle the control circuit measures the amount of ozone in the off gases and compares it with preset values to monitor the progress of the water treatment. This may be based on intermittent readings or continuous readings of the ozone concentration in the off gas or in the head space of container 2.

If the off gas concentration rises as planned (eg. in accordance with a preset range of values or in accordance with a preprogrammed concentration of ozone versus time profile in the off gas or it reaches a preset concentration for the preset time within a preset time period), control circuit 4 detects this as a successful completion of the water treatment process and may then shut down the power to the power light 27 by means of wire 28, the power to the oxygen rich gas source 9 by means of wire 10, and the power to the ozone generator 11 by means of wire 12. It may also cause the water ready light 37 to be illuminated by means of wire 38. Depressing the water dispense button 34 will send a signal to the control circuit 4 by means of wire 35 and will cause the treated water to be decanted from container 2. In one embodiment, the control circuit of this invention may be used in accordance with any method and apparatus to dispense the water from container 2. For example, the water may be poured out of cap 3. Preferably, the water is filtered, such as passing it through a filter 25. This may be achieved by a pump (not shown) or other means known in the art.

In the preferred embodiment of FIG. 1, a sufficient amount of pressure is built up in container 2 to cause the water to exit container 2 and to flow through filter 25. To this end, if the treatment cycle is successfully completed, depressing the water dispense button 34 may send a signal to the control circuit 4 by means of wire 35 which causes the off gas flow control valve 21 to at least partially close, preferably fully close, such as by a mechanical member. Gas, such as from oxygen rich gas source 9, is fed to container 2. This in turn causes pressure to build up within the container 2. When the pressure reaches a preset level (eg. a sufficient amount to cause all of the water in container 2 to pass through filter 25), the water is decanted. In the preferred embodiment, this is achieved by placing a valve 40 which open at the preset pressure in tube 43. Thus the treated water in container 2 will be decanted when the required pressure is reached in container 2. Valve 40 may be a spring loaded check valve. The spring loaded check valve is in communication with the container 2 and the treated water carafe 36. When the check valve is opened, the treated water will flow from the container 2 through tube 43 and through the filter 25 and into the treated water carafe 36. However, it will be appreciated that container 2 may include a pressure sensor which signals control circuit 4 when the preset pressure is reached and control circuit 4 may then send a signal to open valve 40. Further, if gas is supplied to container 2 during the dispensing operation, the preset level may be sufficient, together with the supplement gas introduced into container 2 during the dispensing operation, to cause the treated water to pass through filter 25.

In a further embodiment, if the user depresses the dispense button during the delivery of water to the treated water carafe 36 or optionally during the treatment of water 1 in container 2, then another signal is preferably also sent to the control circuit 4 by means of wire 35. However, since the water treatment is not complete in this case, as a safety feature, the input will cause the off gas flow control valve 21 to be mechanically opened and the oxygen rich gas source 9 to lose power through wire 10 thereby interrupting the dispensing or treatment process. The user may then empty and refill container 2 for another treatment cycle.

Alternately, once a preset amount of time has elapsed during the dispense cycle, the control circuit 4 may interrupt the flow of gas to container 2 (eg. power to the oxygen rich gas source 9 through wire 10 may be terminated) thereby ending the dispensing process. When the user depresses start button 7 in the future, the mechanical off gas flow control valve 21 will be reset to the starting (eg. open) position for the next cycle to proceed.

If the concentration of ozone in the off gas rises too rapidly in relation to preset control values, the control circuit may detect this as a fault and may shut down the power to the power light 27 (for example by means of wire 28), the power to oxygen concentrator 9 through wire 10, and the power to ozone generator 11 through wire 12. It may also cause the system fault light 30 to be illuminated by means of wire 31 to warn the user that the water has not fully treated. As a safety feature in this circumstance, depressing water dispense button 34 will not cause water to be dispensed from container 2 (eg. button 34 may send a signal to the control circuit 4 by means of wire 35 but the input will have no effect as the existence of a system fault precludes permission to dispense the water from the container 2 to the treated water carafe 36). Light 30 will advise the user to manually empty container 2 and that the unit may require servicing.

If the off gas concentration rises too slowly in relation to preset control values (eg. too slowly compared to a preset range of values or slower than a preprogrammed concentration of ozone versus time profile in the off gas or it does not reach a preset concentration for the preset time within a preset time period), control circuit 4 may detect this as a fault and may similarly shut down the power to the power light 27 by means of wire 28, the power to the oxygen concentrator 9 through wire 10, and the power to the ozone generator 11 through wire 12. It may also cause a bad water light 32 to be illuminated by means of wire 33. Also as a safety feature in this circumstance, depressing the water dispense button 34 will send a signal to the control circuit 4 by means of wire 35 but again, the input will have no effect as the existence of an unsatisfactory treatment condition indicated to the user by light 32 being activated precludes water from being dispensed from the container 2 to the treated water carafe 36.

In one embodiment, when the filter has treated a preset number of batches, the control circuit causes a filter light (not shown) to flash thereby warning the user that the filter must be changed soon. After a further preset number of cycles, the control circuit may also cause the filter light to be illuminated warning the consumer that the filter must be changed and that no further water will be dispensed until the filter has been replaced. A sensor 44 (eg. a micro-switch mechanically in contact with filter 25) may be used to signal the control circuit 4 by a wire 45 when the filter has been removed and replaced.

It will be appreciated that many modifications may be made to the spirit of the described invention, the scope of which modifications are limited only by the appended claims. For example lights 27, 30, 32 and 37 may signal a user by issuing any audio, visual or other signal which will advise a user of the specified condition. Each light may be capable of being illuminated to appear different colours so as to send alternating signals to the user thus reducing the total number of lights which are required.

We claim:

1. A domestic method of treating a liquid comprising water with a gas comprising ozone, the method comprising the steps of:
    (a) providing the liquid in a treatment vessel;
    (b) introducing the gas into the vessel to treat the liquid in the treatment vessel to obtain treated liquid;
    (c) increasing the pressure in the treatment vessel; and
    (d) utilizing the increased pressure in the treatment vessel to dispense the treated liquid from the treatment vessel through a carbon filter located downstream from the treatment vessel; and,
    (e) using the increased pressure in the treatment vessel to control a dispensing cycle at a preset pressure level in the treatment vessel.

2. The method as claimed in claim 1 further comprising the step of venting at least a portion of the gas from the treatment vessel during step (b).

3. The method as claimed in claim 2 wherein the pressure in the treatment vessel is increased by reducing the amount of gas which is being vented from the treatment vessel.

4. The method as claimed in claim 1 further comprising the step of venting at least a portion of the gas from the treatment vessel during step (b) and passing at least a portion of the vented gas through the filter prior to dispensing water from the treatment vessel.

5. The method as claimed in claim 1 wherein step (e) comprises automatically dispensing the treated water when the pressure in the treatment vessel reaches a preset level.

6. The method as claimed in claim 1 wherein a first quantity of liquid is treated in the treatment vessel and removed from the treatment vessel before another quantity of liquid is introduced into the treatment vessel whereby the method is performed as a batch process.

7. The method as claimed in claim 1 further comprising the step of treating the liquid with the gas until a prespecified condition is met, the prespecified condition selected from the group:

(a) until a predetermined level of treatment of the liquid is achieved, or (b) for a predetermined time, or (c) until the treatment of the liquid does not match a preset treatment profile.

8. The method as claimed in claim 1 further comprising the step of signalling a user if a predetermined level of treatment of the liquid is not achieved in the predetermined time whereby the user manually empties the treatment vessel.

9. The method as claimed in claim 1 further comprising the step of receiving off gas which passes through the liquid in the treatment vessel in a head space in the treatment vessel, exposing at least a portion of the off gas to an ozone sensor and signalling a user if the concentration of ozone in the off gas is higher than a predetermined amount.

10. The method as claimed in claim 1 further comprising the step of receiving off gas which passes through the liquid in the treatment vessel in a head space in the treatment vessel, exposing at least a portion of the off gas to an ozone sensor and signalling a user if the concentration of ozone in the off gas is lower than a predetermined amount.

11. The method as claimed in claim 1 further comprising the step of monitoring the treatment of the liquid and preventing the liquid from being dispensed from the treatment vessel if a predetermined level of treatment of the liquid is not achieved whereby the user manually empties the treatment vessel.

12. The method as claimed in claim 10 further comprising the step of passing the off gas through the filter to treat the filter prior to dispensing water from the treatment vessel.

13. The method as claimed in claim 1 further comprising the step of monitoring the treatment of the liquid and preventing the liquid from being dispensed from the treatment vessel if the concentration of ozone in the off gas is lower than a predetermined amount.

14. A domestic method of treating water with a gas containing ozone comprising the steps of:

(a) providing the liquid in a treatment vessel;

(b) treating the water in the treatment vessel with ozone to obtain treated water and an off gas;

(c) increasing the pressure in the treatment vessel;

(d) utilizing the increased pressure in the treatment vessel to dispense the treated liquid from the treatment vessel through a carbon filter located downstream from the treatment vessel; and, (e) passing the off gas through the filter to treat the filter prior to dispensing water from the treatment vessel.

15. The method as claimed in claim 14 further comprising the step of signalling a user if a predetermined level of treatment of the water is not achieved.

16. The method as claimed in claim 14 further comprising the step of preventing the water from being dispensed from the treatment vessel if a predetermined level of treatment of the water is not achieved.

17. The method as claimed in claim 14 further comprising the step of venting at least a portion of the gas from the treatment vessel during step (b) and passing the vented gas through the filter prior to dispensing water from the treatment vessel.

18. The method as claimed in claim 14 wherein the pressure in the treatment vessel is increased by reducing the amount of gas which is vented from the treatment vessel.

19. The method as claimed in claim 14 further comprising the step of using the increased pressure in the treatment vessel to engage a dispensing cycle at a preset pressure level in the treatment vessel.

20. A domestic method of treating water with a gas comprising ozone comprising the steps of:

(a) providing water in a treatment vessel;

(b) treating the water in the treatment vessel with ozone to obtain treated water and an off gas;

(c) increasing the pressure in the treatment vessel;

(d) utilizing the increased pressure in the treatment vessel, to dispense the treated liquid from the treatment vessel through a carbon filter located downstream from the treatment vessel; and, (e) preventing the water from being dispensed from the treatment vessel if a predetermined level of treatment of the water is not achieved based on the concentration of ozone in the off gas.

21. The method as claimed in claim 20 further comprising the step of using the increased pressure in the treatment vessel to engage a dispensing cycle at a preset pressure level in the treatment vessel.

22. The method as claimed in claim 20 wherein step (c) comprises preventing the liquid from being dispensed from the treatment vessel if the concentration of ozone in the off gas is lower than a predetermined amount.

23. The method as claimed in claim 20 further comprising the step of venting at least a portion of the gas from the treatment vessel during step (b) and passing the vented gas through the filter prior to dispensing water from the treatment vessel.

24. The method as claimed in claim 20 wherein the pressure in the treatment vessel is increased by reducing the amount of gas which is vented from the treatment vessel.

* * * * *